United States Patent
Durst et al.

(10) Patent No.: US 10,473,599 B2
(45) Date of Patent: Nov. 12, 2019

(54) X-RAY SOURCE USING ELECTRON IMPACT EXCITATION OF HIGH VELOCITY LIQUID METAL BEAM

(71) Applicant: Bruker AXS GmbH, Karlsruhe (DE)

(72) Inventors: Roger D. Durst, Pfinztal (DE); Christoph Ollinger, Karlsruhe (DE)

( * ) Notice: Subject to any disclaimer, the term of this patent is extended or adjusted under 35 U.S.C. 154(b) by 138 days.

(21) Appl. No.: 15/829,068

(22) Filed: Dec. 1, 2017

(65) Prior Publication Data

US 2019/0170670 A1  Jun. 6, 2019

(51) Int. Cl.
| | |
|---|---|
| *H01J 35/00* | (2006.01) |
| *G01N 23/223* | (2006.01) |
| *H01J 35/06* | (2006.01) |
| *H01J 35/22* | (2006.01) |
| *H05G 1/04* | (2006.01) |
| *H05G 1/30* | (2006.01) |
| *G21K 1/06* | (2006.01) |
| *H05G 2/00* | (2006.01) |

(52) U.S. Cl.
CPC .............. *G01N 23/223* (2013.01); *G21K 1/06* (2013.01); *H01J 35/06* (2013.01); *H01J 35/22* (2013.01); *H05G 1/04* (2013.01); *H05G 1/30* (2013.01); *H05G 2/003* (2013.01); *H05G 2/005* (2013.01)

(58) Field of Classification Search
CPC ......... G01N 23/223; G21K 1/06; H01J 35/06; H01J 35/22; H01J 2235/082; H01J 2235/086; H05G 1/30; H05G 2/006
See application file for complete search history.

(56) References Cited

U.S. PATENT DOCUMENTS

| | | | | |
|---|---|---|---|---|
| 3,840,743 A | * | 10/1974 | Tamura | H01J 37/256 250/309 |
| 4,639,301 A | * | 1/1987 | Doherty | H01J 37/3056 204/192.11 |
| 5,243,638 A | | 9/1993 | Wang et al. | |
| 6,531,811 B1 | * | 3/2003 | Kudo | H01J 27/22 313/362.1 |
| 6,995,382 B2 | | 2/2006 | Ziener et al. | |
| 7,929,667 B1 | * | 4/2011 | Zhuang | H05G 2/005 378/119 |
| 9,693,439 B1 | * | 6/2017 | Zhuang | H05G 2/008 |

(Continued)

FOREIGN PATENT DOCUMENTS

JP  2007258069 A  10/2007

*Primary Examiner* — Kiho Kim
(74) *Attorney, Agent, or Firm* — Benoit & Côté Inc.

(57) ABSTRACT

An X-ray source uses excitation of a liquid metal beam of ions or ionized droplets to produce an X-ray output with higher brightness than conventional sources. The beam may be accelerated from a liquid metal source using an extraction electrode. The source may have an emitter tip, and the acceleration of the liquid metal may include field emission from a Taylor cone. An electrostatic or electromagnetic focusing electrode may be used to reduce a cross-sectional diameter of the beam. The liquid metal beam has a relatively high velocity as it does not suffer from flow turbulence, thus allowing for a more energetic excitation and a correspondingly higher brightness. A beam dump may also be used to collect the liquid metal beam after excitation, and may be concave with no direct sight lines to either an electron beam cathode or to X-ray windows of an enclosure for the source.

29 Claims, 3 Drawing Sheets

(56) References Cited

U.S. PATENT DOCUMENTS

2006/0284117 A1* 12/2006 Vanderpot ............ H01J 37/045
                                                250/492.21
2011/0284774 A1    11/2011 Ishihara
2014/0224996 A1*  8/2014 Case ................. H01J 35/14
                                                250/396 ML

* cited by examiner

X-RAY SOURCE USING ELECTRON IMPACT EXCITATION OF HIGH VELOCITY LIQUID METAL BEAM

BACKGROUND OF THE INVENTION

Field of the Invention

This invention relates generally to the field of X-ray beam generation and, more specifically, to the generation of a high brightness X-ray beam using electron impact excitation.

Description of the Related Art

In a large number of fields there is a growing demand for high brightness X-ray sources capable of nanoscale resolution. Examples of such applications include imaging of nanoscale objects (e.g., nanoscale integrated circuits or the interior structure of biological cells), including computerized tomography and phase contrast imaging, as well as X-ray diffraction of nanoscale structures. Conventional X-ray sources with nanoscale resolution exist, but are limited to relatively low brightness.

In order to be used for nano-imaging or nano-diffraction applications, an X-ray source must have a very small focal size, ideally on the order of the size of the object to be imaged or smaller. However, it is also necessary for the source to produce enough X-rays so that sufficient imaging statistics can be achieved in reasonable time. Thus, high brightness is also crucial.

Most current nanoimaging sources are based upon a highly focused electron beam that is focused onto a very thin solid, stationary target (see for example, Sora & Jeong, Jin-Woo & Kim, Jae-Woo & Kang, Jun-Tae & Yeon, Ji-Hwan & Shin, Min-Sik & Kim, Sunghee & Go, Eunsol & Jeon, Hyojin & Chul Choi, Young & Song, Yoon-Ho. (2016), *A field emission nano-focus x-ray source with effective electron beam focusing module*, 1-2. 10.1109/IVNC.2016.7551511). It is crucial that the target in such sources be very thin, on the order of the size of the desired spot focus. This is because the range of high-energy electrons in a solid target is on the order of tens of microns and, thus, even a highly-focused electron beam will produce defocussed X-ray emission in a thick target. FIG. 1, for example, shows simulated 50 keV electron trajectories in a 1 μm thick tungsten target. It can be seen that the electron trajectories are strongly scattered such that X-rays will be produced from a volume on the order 1000 nm, on the order of the thickness of the target.

FIG. 2 shows a similar calculation for a tungsten target which is only 100 nm thick. In the thinner target there is less electron scattering and thus the X-ray emission will be produced in a volume on the order of 100 nm. Therefore, in general, we can say that the thickness of the target for an X-ray source must be comparable to or smaller than the areal size of the desired X-ray emission. In particular, for nanofocus tubes the target thickness must be on the order of 100 nm or less.

Another key consideration for a nanofocus X-ray source is brightness. X-ray brightness is simply proportional to the electron beam power load. However, the process of electron impact excitation is rather inefficient, typical only 1-2% of the energy of the incoming X-ray beam is converted to X-rays. Because of this, all such electron-impact sources must be designed to deal with the majority of the incident electron beam energy which is converted to heat ((E. Krestel, Imaging Systems for Medical Diagnostics (Siemens, Berlin, 1990)). If the power load exceeds certain limits, the anode melts and is destroyed (D E Grider et al 1986 *J. Phys. D: Appl. Phys.* 19 2281). Therefore, the brightness of any source based on electron impact excitation of X-rays in a solid target will be limited by the thermal load.

In a conventional nanofocus tube, a thin layer of a target metal is coated on an X-ray transparent substrate, often diamond or beryllium, as shown in FIG. 3. In this configuration, an X-ray transparent substrate 11 acts as a mechanical support for a thin metal target layer 13, and also serves as a heat sink to remove waste heat from the target. X-rays 17 are excited by a focused electron beam 15 and are transmitted through the transparent substrate 11. This type of stationary anode has been shown to achieve a power loading on the order of 10 kW/mm² which equates to an X-ray brightness on the order of $10^{11}$ X-rays/mm²-mrad²-sec. This relatively low brightness in turn implies that nanoresolution X-ray imaging with such a low power tube would require long exposure times (typically on the order of minutes).

In certain prior art systems, the achievable power loading has been significantly improved by rotating the anode. Such a rotation causes the heat load from the electron beam to be spread over the surface of the anode (W. J. Osterkamp, Philips Res. Rep. 3, 303 (1948)). In such a case, the achievable power loading scales as:

$$p_0 \propto \Delta T_m \left(\frac{\omega R}{b}\right)^{1/2}$$

where $p_0$ is the power loading, $\Delta T_m$ is the maximum allowable temperature rise, b is the width of the electron focal spot, ω is the angular rotation velocity and R is the anode radius.

As is known in the art, the maximum temperature rise, $\Delta T_m$ is a function of the anode material. At the limit, it is bounded by the melting point of that material. However, in most cases the anode surface will be damaged by the mechanical micro-stresses induced by rapid thermal cycling and, thus, lower values of $\Delta T_m$ are typically achieved in practice. For example, the bulk of the anode material used is typically copper (chosen for its high thermal conductivity). A copper anode typically tolerates a temperature rise of less than 500° C., even though its melting point is 1083° C. Some proprietary copper alloys can tolerate somewhat higher temperature rises and, thus, higher power loading.

It is known that the power loading can be increased at higher rotation velocities (ωR). Present day rotating anodes typically operate at angular rotation frequencies that can reach up to about 10,000 rpm. These sources can therefore sustain a steady state power loading of up to 30 kW/mm², three times higher than the best stationary tubes. However, all conventional rotating anodes are operated in reflection mode with thick X-ray targets. There is currently no rotating anode technology that could be directly applied to a thin target for nano-resolution imaging or diffraction.

In order to further increase the power loading (and thus the X-ray brightness), it has been recently proposed to use a freely propagating metal jet as the anode in an X-ray source (M. Otendal, T. Tuohimaa, U. Vogt, and H. M. Hertz (2008), *A 9 keV electron-impact liquid-gallium-jet x-ray source*, Rev. Sci. Instrum., 79). The metal jet source follows approximately the same scaling relationship as the equation above, with the exception that the temperature rise is limited by the boiling point of the liquid metal target (e.g., ΔT=500° K for Gallium). Also, a freely propagating jet of liquid metal can achieve surface velocities significantly higher than is possible with a solid rotating anode, and can currently reach up to about 100 m/sec. This, in turn, allows steady state power loading of up to about 100 kW/mm², which is several times higher than is possible with solid target rotating anodes. The smallest focus size reported for such a metal jet source is on the order on 5 µm. However, this is too large for most nano-imaging or nano-diffraction applications. For nano-imaging or nano-diffraction one would prefer to use a source with a spot size on the order of 100 nm or smaller. However, a source with such a small spot size has not been reported.

SUMMARY OF THE INVENTION

In accordance with the present invention, an X-ray generating apparatus is provided that uses a beam of liquid metal ions or ionized droplets excited by an excitation beam, such as an electron beam or a laser beam. A source of liquid metal is provided, and an electric field generator is used to electrostatically accelerate the liquid metal from the source to form a liquid metal beam in a first direction. An excitation beam source outputs the excitation beam that intersects the liquid metal beam and excites the liquid metal therein to produce X-rays.

The system may be arranged so that the temperature of the liquid metal beam after excitation is above a vaporization temperature of the liquid metal while remaining below an ionization temperature thereof. The electric field generator may make use of an extraction electrode that has a voltage potential relative to the liquid metal source, and that may have an orifice through which the liquid metal beam passes. One or more ion focusing lenses may also be used to focus the liquid metal beam. Such a focusing lens may be an electrostatic lens or an electromagnetic lens. In an exemplary embodiment, the focusing lens focuses the liquid metal beam to a cross-sectional diameter of less than 1 µm, and may focus the beam to a cross-sectional diameter of less than 100 nm.

In one embodiment, the liquid metal includes at least one of gallium or indium, and the liquid metal source may use a capillary through which the liquid metal flows. The capillary may have an emitter tip of a material such as tungsten, and may have a narrowing, conical profile in the first direction. With or without such an emitter tip, the liquid metal from the liquid metal source may be accelerated by field emission from a Taylor cone.

In another embodiment, a beam dump is used that collects the liquid metal beam after intersection by the electron beam. The beam dump may be concave such that it has no direct sight lines to an X-ray window of a housing surrounding the source, or to an electron beam cathode used in generating the electron beam. The beam dump may also be provided with a relative voltage potential that attracts the liquid metal beam. The system may also be configured so that the liquid metal beam source provides a plurality of liquid metal beams in the first direction that propagate adjacent to one another.

DETAILED DESCRIPTION

Figure 4:
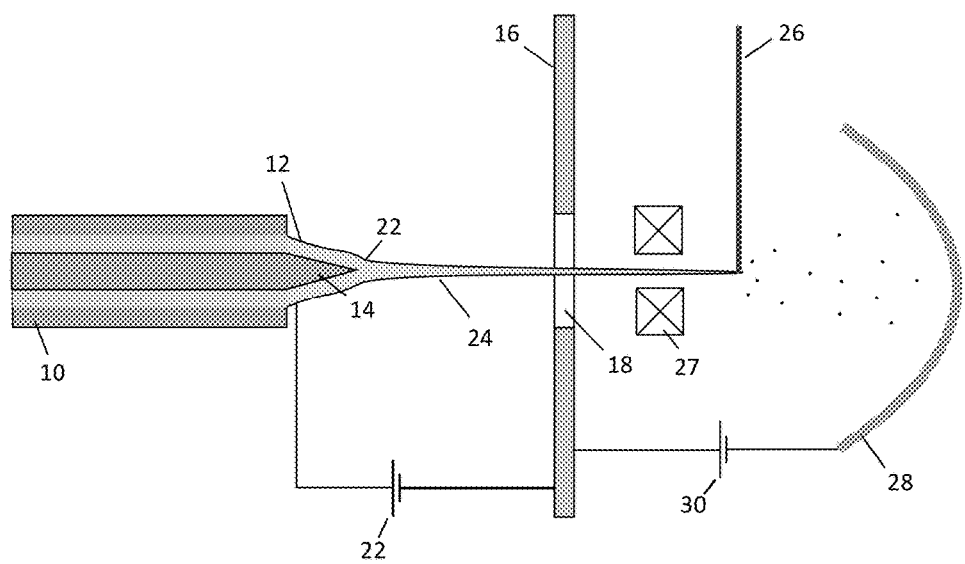
FIG. 4 is a schematic view of a liquid metal source according to the present invention.

Shown in FIG. 4 is an exemplary embodiment of the invention that uses a liquid metal ion source (LMIS) to create a beam of charged liquid metal ions that serves as the anode for an electron impact X-ray source. Such ion sources have been used in the past for applications such as ion implantation and focused ion beam instruments. In the present invention, however, the LMIS concept is adapted to an X-ray source application, and is used to provide liquid metal for an electron beam target. Unlike the liquid metal jet sources of the prior art, the LMIS is not subject to the issues of turbulent flow, which limit the flow velocity, and therefore the power loading, of those prior art sources. Rather, the invention provides a beam of metal ions, or partially ionized metal droplets, that can reach velocities of up to $10^5$ m/sec, which is over two orders of magnitude higher than that achieved in current generation liquid metal sources. This higher velocity, in turn, provides a much higher permissible power loading and, therefore, the capacity to generate an X-ray beam of much higher brightness.

Figure 1:
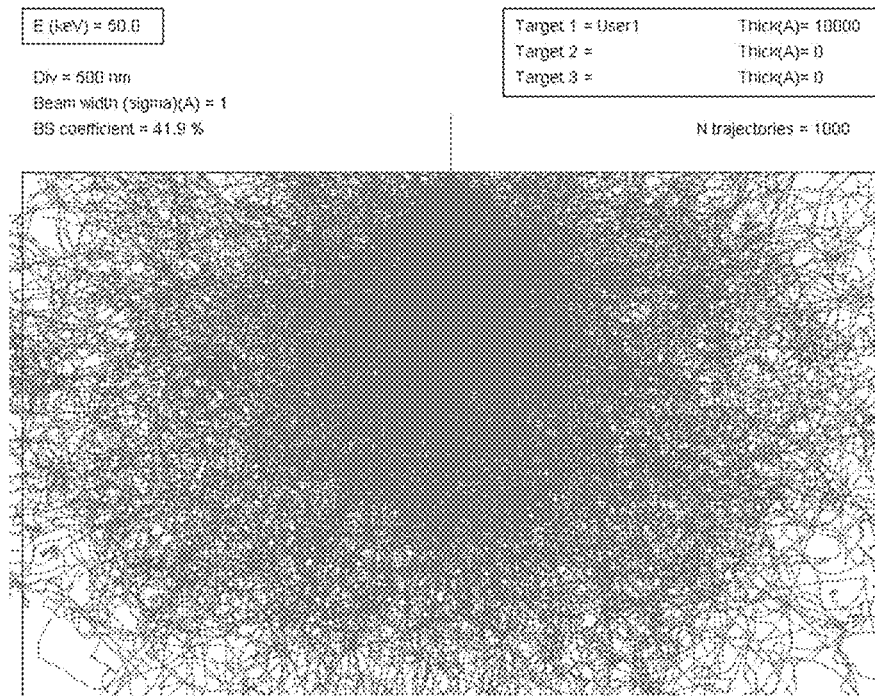
FIG. 1 is a schematic view showing simulated 50 keV electron trajectories in a 1 µm thick tungsten target.
Figure 2:
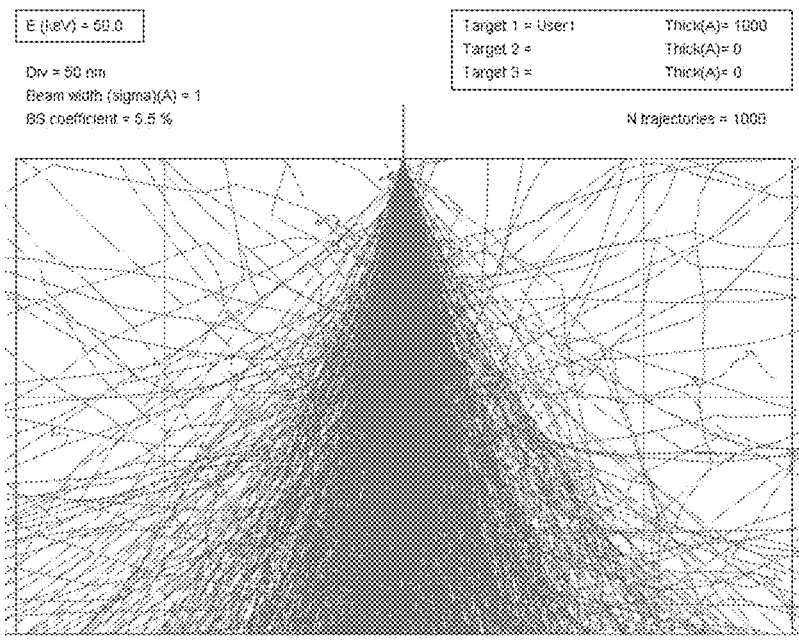
FIG. 2 is a schematic view showing simulated electron trajectories in a 100 nm thick tungsten target.
Figure 3:
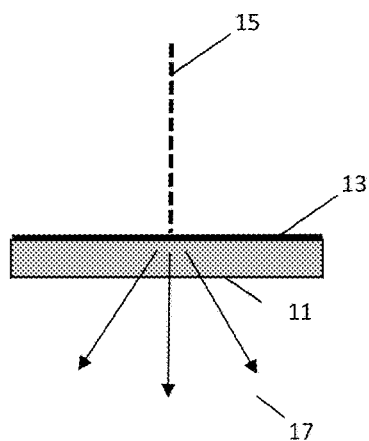
FIG. 3 is a schematic representation of a conventional nanofocus X-ray tube having a thin metal target layer coated onto an X-ray transparent substrate.

The configuration shown in FIG. 4 includes a capillary 10 through which a liquid metal 12 flows. In principle, any liquid metal may be used, but either Gallium or Indium (or alloys thereof) are preferred choices for their low melting points and low vapor pressure, and because the characteristic radiation that they emit in response to electron bombardment falls within a range that is useful for a variety of diffraction and imaging applications. The capillary 10 in the FIG. 1 embodiment includes an emitter 14, which is an elongated surface around which the liquid metal flows, and which narrows to a point to form a conical shape at the output of the capillary. The emitter 14 of this embodiment uses a tungsten tip, but those skilled in the art will recognize that other materials may be used as well. In addition, while the emitter 14 is used in the FIG. 4 embodiment, it is also possible to form a Taylor cone at the end of a capillary that has no such emitter.

In front of the emitter 14 is an extraction electrode 16 that may be a conductive plate and that has an orifice 18 that is aligned with the emitter 14 along a longitudinal axis of the capillary 10. A voltage source 20 is connected to the emitter 14 and the extraction electrode 16, forming an electric field therebetween that draws the liquid metal from the emitter 14 toward the electrode orifice 18. The electric field pulls the liquid metal at the emitter 14 into a Taylor cone 22, from which the liquid metal is extracted. At lower voltages, single ions are emitted from the Taylor cone via field emission at currents of up to about 10 µA. At higher voltages, there will be a beam of small droplets, typically on the order of 1 µm diameter or less, each carrying a finite charge, where the charge ratio (in ions per total atoms) is typically on the order of 0.1. In an exemplary embodiment, the current is generally maintained below 10 µA so that a laminar ion beam is produced that, in turn, produces a constant X-ray intensity.

However, in other applications, it may be desirable to run at a higher current and, therefore, at a higher X-ray flux.

The liquid metal beam 24 traverses the orifice of the extraction electrode 16, and encounters excitation beam 26 which, in this embodiment, is an electron beam. Alternatively, the excitation beam 26 can be a laser beam, which may be used, for example, for the generation of soft X-rays. The diameter of the ion beam may be controlled via electrostatic or electromagnetic optics, such as ion lens 27, to achieve the desired ion beam diameter. Electron bombardment of the liquid metal beam results in the emission of hard X-rays that may be used in a variety of different X-ray analysis systems. The liquid metal ion beam may be focused to 1 μm or less using focusing ion lens 27, and the velocity of the moving metal may be up to 100 km/sec, which is three orders of magnitude higher than is possible with a conventional liquid metal jet. This higher velocity allows for a more intense bombardment with the electron beam and, consequently, higher power loading and an X-ray brightness more than an order of magnitude higher. Focusing lens 27 may be any of a number of different types of lens types known in the art, some of which are described, for example, in Szilagyi, Miklos. *Electron and Ion Optics*, Springer Science & Business Media, 2012.

As a result of excitation by the electron beam, the liquid metal beam will be strongly scattered. It is desirable to prevent the liquid metal ions from depositing randomly in the chamber, as this can lead to coating of the exit windows, which would reduce the X-ray output due to self-absorption, and/or the cathode of the electron source, which would reduce its efficiency and/or lifetime. Because the beam atoms are ionized, a beam dump 28 is used that is negatively biased relative to the extraction electrode 16 to collect the scattered ions and thus reduce the number of liquid metal ions that might otherwise be deposited on an exit window or on the electron source cathode. Biasing of the beam dump 28 may be achieved by locating a voltage source 30 between the extraction electrode 16 and the beam dump. Although different materials may be used, the beam dump 28 of the present embodiment is made of a material, such as titanium, that will not degrade the vacuum or cause a health risk when deposited on other parts of the vacuum chamber.

Although the liquid metal ions are collected on the surface of the beam dump 28, because of the relatively high energy of the ion beam, atoms will nonetheless be sputtered from the beam dump 28, which could still lead to deposition of the sputtered atoms on an exit window or the electron source cathode. The geometry of the beam dump is therefore made so that there are no direct lines of sight to any such surface where deposition would be undesirable. This is accomplished in the example of FIG. 4 by making the beam dump concave with an axis of rotation facing back towards the ion beam. This ensures that, for most of the sputtered atoms from the beam dump, it will not be possible for them to be deposited on the surface of either the X-ray window(s) or the electron beam cathode.

For a system like that shown in FIG. 4, a source operated in the singly charged ion mode has a beam of liquid metal atoms, the real density of which may be described as:

$$\rho_a A = I/vQ$$

where $\rho_a$ is the average density of liquid metal atoms in the beam (in atoms/m³), A is the cross-sectional area of the beam (in m²), v is the beam velocity, and Q is the charge per droplet in the beam. The velocity of the droplets may be given as:

$$v = \sqrt{\frac{2QV}{M}}$$

where M is the mass of the ions (or droplets) and V is the voltage applied between the emission tip and the extraction electrode. Assuming that the entire beam is illuminated by the exciting electron beam, and that there is negligible self-absorption of X-rays, the X-ray emission is given by:

$$E = \eta \rho_a A v = \eta \frac{I}{Q}$$

where E is the X-ray emission in X-rays per second, and η is the X-ray efficiency (on the order of 0.01). Similarly, the brightness of the source may be expressed as:

$$B = \frac{E}{4\pi A} = \frac{I}{4\pi QA}$$

In the case of a gallium liquid metal source operating in single ion mode (i.e., where the beam consists of singly charged ions focused to a diameter of 1 μm), and a current of 10 μA, the velocity of the beam is 100 km/sec, the X-ray emission is $6\times10^{11}$ X-rays per second, and the brightness is on the order of $2\times10^{13}$ X-rays/mm²-sec. Notably, this brightness is approximately two orders of magnitude higher than currently-available, conventional solid target nanofocus tubes. Moreover, by using an axial magnetic lens, such as focusing ion lens 27 shown in FIG. 4, the ion beam can be focused to 0.1 μm, and the achievable brightness increases to $2\times10^{15}$ X-rays/mm²-sec, which is more than five orders of magnitude brighter than a conventional solid target nanofocus tube, comparable in brightness to synchrotron beamline sources.

In the case of gallium liquid metal source operating in droplet mode, with a current of 100 μA and a beam cross section of A=10 pmt, approximately 10% of the gallium atoms will be charged, (so that Q/M=1.5×10⁵ C/Kg), and the droplet velocity is reduced to 40 km/sec. Assuming again that the entire beam is excited and the self-absorption is negligible, the emission is E=$6\times10^{13}$ X-rays/sec and the brightness is $2\times10^{13}$ X-rays/mm²-sec-mrad². That is, this configuration emits more total X-rays (because the area density of liquid metal atoms is higher), but the brightness is not improved relative to the single ion mode.

Figure 5:
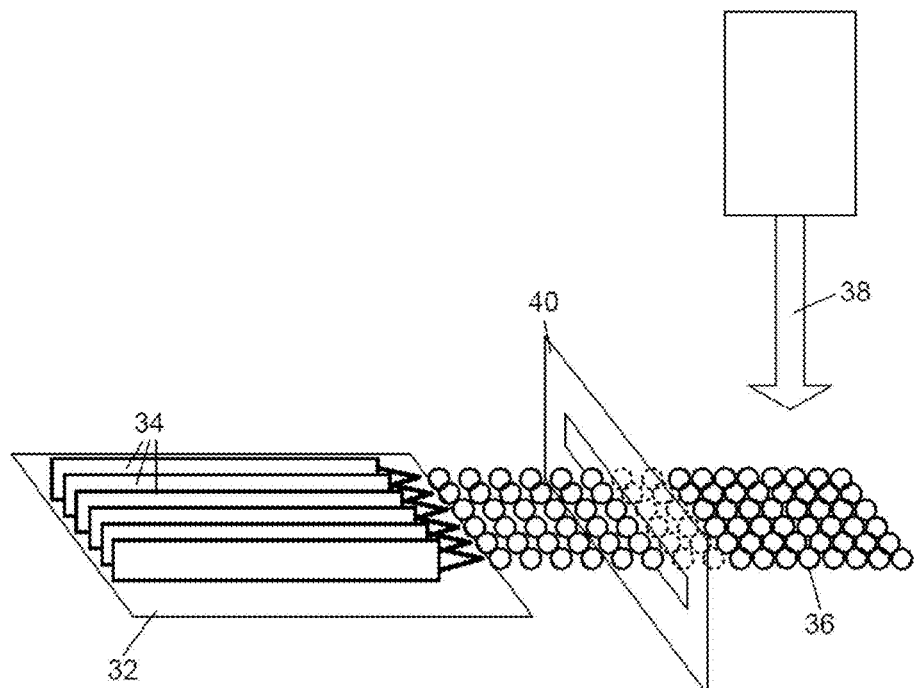
FIG. 5 is a schematic view of an embodiment of the invention that uses multiple liquid metal beams adjacent to one another.

While the example shown in FIG. 4 makes use of a single LMIS, it is also possible to create an X-ray source that combines more than one LMIS to increase the X-ray flux. For example, a linear array 32 of LMIS 34 could be used, as shown schematically in FIG. 5. When correctly positioned relative to each other, the array will produce a "sheet" 36 of liquid metal ion beams that may be drawn toward an electron beam 38 by an elongate extraction electrode 40. An arrangement such as this can improve the apparent brightness of a resulting X-ray signal that is emitted along a relatively low take-off angle.

The foregoing example involves the excitation of hard X-ray radiation via an incident electron beam that interacts with the liquid metal ion beam. However, it is also possible to instead illuminate the ion beam with laser radiation in which case VUV or soft X-ray radiation may be produced.

In addition to providing an X-ray source with higher brightness than prior art systems, the present invention has some other advantages. For example, the system has no moving parts, and therefore offers higher reliability than conventional liquid metal jet sources (which typically require high pressure pumps to drive the liquid metal through a nozzle). Moreover, while the X-ray emission in a conventional liquid metal source is limited to the 2π steradians facing the electron beam (since the anode is not transparent to X-rays), the liquid ion beam of the present invention is transparent to X-rays, and X-rays are therefore emitted into nearly 4π steradians. This is demonstrated by the schematic diagram of FIG. 6.

Figure 6:
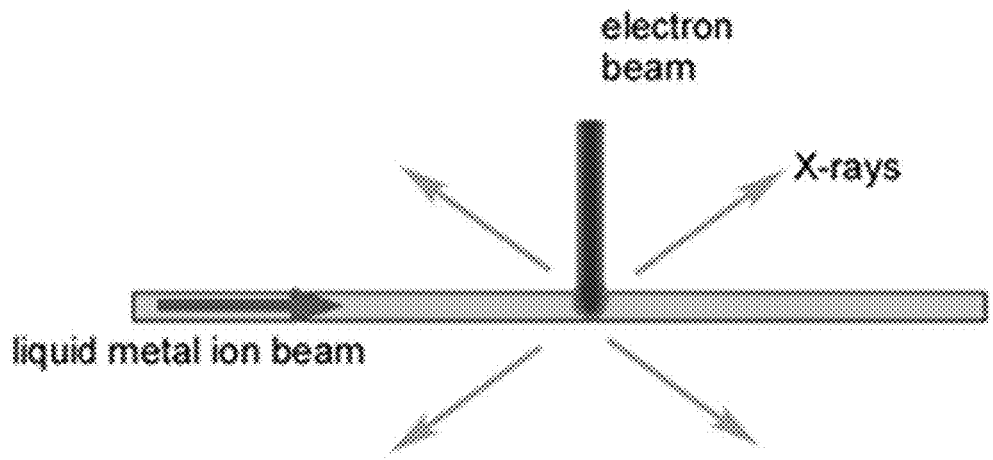
FIG. 6 is a schematic view of X-ray generation using electron bombardment of a liquid metal ion beam.

In a conventional liquid metal jet with a diameter of 10 μm or larger, the jet is at liquid density, and the electron beam will typically only penetrate partially into the jet, typically some tens of microns depending on the electron energy. Because of this, all the X-rays are emitted from a thin layer at the surface of the jet and the jet is not transparent to X-rays so that no radiation is emitted in the direction of the X-ray beam. In contrast, a liquid metal ion beam, as shown in FIG. 6, that is focused to a small size on the order of 1 μm (and preferably less than 100 nm) consists of a propagating cloud of metal ions. The effective density of this cloud is on the order of 10-100 times lower than the liquid density which, combined with the small diameter of the beam, means that the ion beam is effectively transparent to X-ray radiation. Thus, the range of the exciting electrons and the escape depth of the X-rays are correspondingly longer, and the entire beam is simultaneously excited and emits X-rays in all directions, as indicated in the figure. These additional directions of X-ray emission allow, in principle, more instrumentation ports to be installed.

Another advantage of this type of source is that the required amount of liquid metal is relatively small. In a conventional liquid metal source, the liquid metal must be collected, cooled, filtered and recycled, which adds significant complexity and cost. With the present invention such recycling is also possible but, in many cases, is not necessary because the use of liquid metal is much lower. For example, running at 10 μA, the source would require only about 1 ng of liquid metal per second of operation. This means that, at most, the source would require less than a gram of gallium per year of operation. Because of this, it is not necessary to collect the liquid metal and recycle it, as is done for example in present-day liquid metal jet sources. Rather, the source can start with a small amount (e.g., several grams) of liquid metal which will be enough to supply the required ion beam for several years of operation. The elimination of the liquid metal recycling system significantly reduces the cost and complexity of the source compared to conventional liquid metal jets. In this case the beam dump as described above can be used to chemically sequester the gallium or indium. After several years of operation, the entire tube would then be recycled.

Due to the small spatial extension of the x-ray focal spot, especially in single ion beam mode with magnetic focusing, a significant increase of the spatial coherence length of the source is also achieved. Following the Van Cittert-Zernike theorem, the spatial coherence length can be defined as:

$$L_s = \frac{z\lambda}{2\pi d}$$

with z being the distance from the source, λ the wavelength of the x-ray radiation and d the spatial extension of the source. In the case of a gallium liquid metal ion source operating in single ion mode and focused down to 0.1 μm, the spatial coherence length in a distance of 1 m from the source is approximately 200 μm. With the brightness value given above, the achievable coherent flux at 1 m distance can be estimated to be >2×10$^4$ x-ray/sec, allowing coherent x-ray experiments without the need to use large scale facilities.

The invention claimed is:

1. An X-ray generating apparatus comprising:
   a liquid metal beam generator that electrostatically accelerates liquid metal ions or ionized droplets from a liquid metal source to form a liquid metal beam in a first direction having a minimum velocity of 40 km/s; and
   an excitation beam source that outputs an excitation beam that intersects the liquid metal beam and excites the liquid metal therein to produce X-rays.

2. An apparatus according to claim 1 wherein the liquid metal beam generator comprises an extraction electrode separated from the liquid metal source that draws the liquid metal beam in the first direction.

3. An apparatus according to claim 2 wherein the liquid metal beam passes through an orifice in the extraction electrode.

4. An apparatus according to claim 1 wherein the liquid metal from the liquid metal source is accelerated by field emission from a Taylor cone.

5. An apparatus according to claim 1 further comprising at least one ion focusing lens that focuses the liquid metal beam.

6. An apparatus according to claim 5 wherein the ion focusing lens is an electrostatic lens.

7. An apparatus according to claim 5 wherein the ion focusing lens is an electromagnetic lens.

8. An apparatus according to claim 5 wherein the ion focusing lens focuses the liquid metal beam to a cross-sectional diameter of less than 1 μm.

9. An apparatus according to claim 1 wherein the liquid metal comprises at least one of gallium and indium.

10. An apparatus according to claim 1 further comprising a beam dump that collects the liquid metal beam after intersection by the electron beam.

11. An apparatus according to claim 10 wherein the beam dump is concave.

12. An apparatus according to claim 10 wherein the beam dump has a relative voltage potential that attracts the liquid metal beam.

13. An apparatus according to claim 1 wherein the liquid metal source comprises a capillary through which the liquid metal flows.

14. An apparatus according to claim 13 wherein the capillary further comprises a conical, tapered emitter tip on the surface of which the liquid metal flows.

15. An apparatus according to claim 14 wherein the emitter tip comprises tungsten.

16. An apparatus according to claim 1 wherein the excitation beam is an electron beam.

17. An apparatus according to claim 1 wherein the excitation beam is a laser beam.

18. An apparatus according to claim 1 wherein the liquid metal beam is a first liquid metal beam, and wherein the liquid metal beam generator is configured to accelerate a plurality of liquid metal beams in the first direction that propagate adjacent to one another.

19. An X-ray generating apparatus comprising:
a liquid metal source at which a Taylor cone of liquid metal may be formed;
an extraction electrode that accelerates liquid metal ions or ionized droplets from the liquid metal source to form a liquid metal beam in a first direction;
an ion focusing lens that focuses the liquid metal beam to a cross-sectional diameter of less than 1 µm;
an excitation beam source that outputs an excitation beam that intersects the liquid metal beam and excites the liquid metal therein to produce X-rays; and
a beam dump that collects the liquid metal beam after intersection by the excitation beam.

20. A method of generating X-rays, the method comprising:
providing a source of liquid metal;
accelerating liquid metal ions or ionized droplets electrostatically from the liquid metal source to form a liquid metal beam in a first direction having a minimum velocity of 40 km/s; and
transmitting an excitation beam that intersects the liquid metal beam and excites the liquid metal therein to produce said X-rays.

21. A method according to claim 20 wherein accelerating the liquid metal ions or ionized droplets comprises generating an electric field with an extraction electrode separated from the liquid metal source.

22. A method according to claim 20 wherein accelerating the liquid metal ions or ionized droplets from the liquid metal source comprises accelerating the liquid metal ions or ionized droplets by field emission from a Taylor cone.

23. A method according to claim 20 further comprising collecting the liquid metal beam in a beam dump after intersection by the excitation beam.

24. A method according to claim 20 wherein providing a source of liquid metal comprises providing a capillary through which the liquid metal flows.

25. A method according to claim 24 wherein the capillary comprises an emitter tip with a narrowing profile in the first direction.

26. A method according to claim 20 further comprising focusing the liquid metal beam with an ion focusing lens.

27. A method according to claim 26 wherein the ion focusing lens is an electrostatic lens.

28. A method according to claim 26 wherein the ion focusing lens is an electromagnetic lens.

29. A method according to claim 26 wherein the ion focusing lens focuses the liquid metal beam to a cross-sectional diameter of less than 1 µm.

* * * * *